United States Patent [19]
Hori et al.

[11] 4,262,157
[45] Apr. 14, 1981

[54] DECARBOXYLATION PROCESS

[75] Inventors: Yuji Hori, Saga; Yoshiaki Nagano; Hiroshi Taniguchi, both of Fukuoka, all of Japan

[73] Assignee: Abbott Laboratories, North Chicago, Ill.

[21] Appl. No.: 134,400

[22] Filed: Mar. 27, 1980

[51] Int. Cl.$^3$ .................................................. C07C 1/20
[52] U.S. Cl. .................................. 585/733; 260/465.1; 568/630; 568/671; 568/840; 570/201; 585/437; 585/469; 564/183; 564/215; 568/939; 568/947
[58] Field of Search ................................ 585/638, 733

[56] References Cited

U.S. PATENT DOCUMENTS

| | | | |
|---|---|---|---|
| 3,476,803 | 11/1969 | Pine | 585/733 |
| 3,729,520 | 4/1973 | Rutzen et al. | 585/733 |
| 3,769,244 | 10/1973 | Hashimoto et al. | 260/2.5 AC |
| 3,814,707 | 6/1974 | Möller et al. | 260/2.5 AC |

OTHER PUBLICATIONS

ACS Abstract (Apr. 1-6, 1979) No. 586.

*Primary Examiner*—Curtis R. Davis
*Attorney, Agent, or Firm*—Paul D. Burgauer; Robert L. Niblack

[57] ABSTRACT

Decarboxylation of carboxylic acids using diazabicycloalkenes and, if desired, also a simple copper salt, as the means for decarboxylation.

12 Claims, No Drawings

DECARBOXYLATION PROCESS

DETAILED DESCRIPTION OF THE INVENTION

Previously, the process of heating sodium salts of fatty acids in the presence of sodium hydroxide at 360° to 380° C. was known as the decarboxylation process for fatty acids. That process is useful for obtaining very short chain fatty acids, such as those having 1–3 carbon atoms. However, in the case of relatively longer carbon chains, for example 6 or more, the yield of decarboxylated products having the corresponding carbon chain is only 12% or less, as shown in J. Am. Chem. Soc., 72, 1849 (1950). According to that source, the decarboxylating product is decomposed into smaller molecular fractions caused by pyrolysis during the decarboxylation process.

It has now been found that carboxylic acids can be decarboxylated by combining one molar equilalent of a carboxylic acid with 0.8 to 3 molar equivalents of a diazabicycloalkene (hereinafter referred to as DBA) and 0 to 20 molar equivalents of a simple copper salt at a temperature of 0° to 400° C. for a period of 0.1 to 50 hours.

The above DBA is depicted by the structure

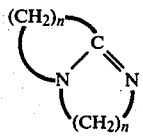

wherein n is an integer from 2 to 11, m is an integer from 2 to 6 and each ring may carry one or more lower alkyl radicals. The ranges for the reaction temperature are preferably 300° to 380° C. for saturated fatty acids, 200° to 300° C. for unsaturated fatty acids or for carboxylic acids whose carboxyl radical is bonded directly to a homocyclic or heterocyclic ring, and room temperature to 300° C. for substituted carboxylic acids. The preferred amount of DBA is 1 to 2 equivalents: Higher amounts will not appreciably benefit the process, and with amounts below 1 molar equivalent of DBA, a correspondingly lower amount of the carboxylic acid is decarboxylated. Reaction periods are preferably between 0.3 and 7 hrs.

Usually, no additional reaction takes place after about 7 hrs. Of course, when operating at higher temperatures, shorter reaction times, such as 20 min. can be used and vice versa. When in addition to the DBA, one uses a copper salt as an additional reactant or catalyst, its amount is preferably chosen between 0.7 and 5 molar equivalents, although larger amounts, such as up to 20 molar equivalents can be used.

The optional copper salts employed in this process are cuprous salts or cupric salts. The cuprous salts are cuprous chloride, bromide or iodide; the cupric salts comprise cupric chloride, bromide, sulfate, nitrate and acetate. The cuprous salts are preferred, and the most preferable ones are cuprous chloride and cuprous bromide.

The DBA's of structure I can be illustrated by the following representative compounds:
1,5-diazabicyclo(4,2,0)octene-5;
1,8-diazabicyclo(7,2,0) undecene-8;
1,4-diazabicyclo(3,3,0)octene-4;
3-methyl-1,4-diazabicyclo(3,3,0)octene-4;
3,6,7,7-tetramethyl-1,4-diazabicyclo(3,3,0)octene-4;
7,8,8-trimethyl-1,5-diazabicyclo(4,3,0)nonene-5;
1,8-diazabicyclo(7,3,0) dodecene-8;
1,7-diazabicyclo(4,3,0)nonene-6;
1,5-diazabicyclo(4,4,0)decene-5;
1,8-diazabicyclo(7,4,0) tridecene-8;
1,8-diazabicyclo(5,3,0)decene-7;
9-methyll,8-diazabicyclo(5,3,0)decene-7;
1,8-diazabicyclo(5,4,0) undecene-7;
1,6-diazabicyclo(5,5,0)dodecene-6;
1,7-diazabicyclo(6,5,0)tridecene-7;
1,8-diazabicyclo(7,5,0) tetradecene-8;
1,10-diazabicyclo(7,3,0)dodecene-9;
1,10-diazabicyclo(7,4,0)tridecene-9;
1,14-diazabicyclo (11,3,0)hexadecene-13;
1,14-diazabicyclo(11,4,0) heptadecene-13.

The carboxylic acids include a large variety of simple fatty acids or substituted carboxylic acids wherein the substituent or substituents are stable. Many of these are listed here as illustrations:

Saturated fatty acids having a straight or branched chain of 2 to 32 carbon atoms, for example, acetic acid, propionic acid, butyric acid, valeric acid, isovaleric acid, caproic acid, caprylic acid, capric acid, lauric acid, tridecyclic acid, myristic acid, palmitic acid, stearic acid, arachic acid, behenic acid and montanic acid;

Unsaturated fatty acids having a straight or branched chain of 3 to 22 carbon atoms, for example, acrylic acid, methacrylic acid, crotonic acid, isocrotonic acid, undecylenic acid, oleic acid, elaidic acid, erucic acid, linoleic acid, linolenic acid, arachiodonic acid and stearolic acid;

Aromatic mono-carboxylic acids such as benzoic acid, toluic acid and naphthoic acid;

Heterocyclic mono-carboxylic acids, for example, furan carboxylic acid, thiophene carboxylic acid, nicotinic acid and isonicotinic acid;

Aliphatic polycarboxylic acids and their partial esters such as malonic acid, succinic acid, glutaric acid, adipic acid, azelaic acid, or unsaturated polycarboxylic acids such as fumaric acid, maleic acid and dimer acid;

Cyclic polycarboxylic acids such as phthalic acid, isophthalic acid, terephthalic acid, naphthalene dicarboxylic acid, benzene tricarboxylic acids, trimellitic acid and the like, benzene tetracarboxylic acids, pyromellitic acid and the like;

Partial alkyl esters (C=1 to C=20, saturated or unsaturated) of aliphatic polycarboxylic acids or partial allyl esters of the above acids such as succinic acid mono-ethyl ester, adipic acid mono-butylester and partial alkyl (shown as the above) esters or partial allyl esters of cyclic polycarboxylic acids, such as phthalic acid mono-alkyl esters, phthalic acid monoallyl esters, trimellitic acid dialkyl esters, pyromellitic acid trialkyl esters, isophthalic acid monoallyl esters, terephthalic acid monoallyl esters;

Substituted carboxylic acids wherein one or more hydrogen atom (other than that of the carboxyl group) is replaced by aryl, styryl, alkoxy, allyloxy, phenoxy, hydroxy, nitro, cyano, halogen, acyl, benzoylamino, sulfonic acid radicals or their salt radicals such as phenylacetic acid (mono-, di- and tri-) cinnamic acid, diphenylene acetic acid (fluorene-9-carboxylic acid), styryl acrylic acid, styryl acetic acid and the like, methoxy benzoic acid (o-, p- or m-), phenoxy acetic acid, phenoxy propionic acid, chlorobenzoic acid (p-, m- or o-), 2,4,6-trichloro acetic acid, 2-methyl4-chlorophenoxy acetic acid, cyclohexanoyl benzoic acid, acetoacetic acid, benzoylacetic acid, ricinoleic acid, hydroxy stearic acid, salicylic acid, lactic acid, citric acid, nitrobenzoic acid (o-, m-, p-), cyanoacetic acid, benzoylamino fatty acids, such as hippuric acid and the like, sulfonated fatty acids, such as sulfonated $C_{16}$-fatty acid and the like.

Also, resins having carboxyl radicals such as polymerized resins having carboxyl radicals (acrylic resin) and condensed resins having carboxyl radicals (polyester resin having carboxyl radical) are included in the present invention. The above carboxylic acid can be used in the form of mixture containing two kinds of carboxylic acids, too.

The DBA's of the present invention wherein n is 3 to 5 and m is 2 to 3 are preferred; especially the compound wherein n equals 5 and m equals 3 produces outstanding results. While all the DBA's can be used alone, the combination thereof with a copper salt is preferred where the carboxylic acid radical to be removed is bonded directly to a homocyclic or heterocyclic ring.

The reaction can be carried out by adding the carboxylic acid to a DBA or vice versa, and if desired, adding a copper salt to the reaction mixture, stirring and transmitting an inert gas. In general, the reaction is carried out under atmospheric pressure, but reduced pressure is equally accepted, as well as operating under an inert gas blanket, for instance argon or nitrogen. Solvents may be used with the reaction mixture; an aprotic polar solvent, such as dimethylformamide, dimethylacetamide and dimethylsulfoxide, is preferred.

After completion of the reaction, the decarboxylated product can be isolated by applying well-known methods, such as distillation, solvent extraction, recrystallization or column chromatography, depending on the physical state of the product to be obtained. For instance, gases and liquids having a boiling point below 360° C. can be distilled, high boiling compounds are isolated by chromatography, etc. The isolated decarboxylated product can be identifed by using analytical methods such as gas chromatography, mass spectrography, infrared spectra, nuclear magnetic resonance analysis and so on.

During the reaction, the evolved carbon dioxide from the decarboxylation reaction forms a complex of DBA. $CO_2$. This complex also can be isolated (for instance the 1,8-diazabicyclo(5,4,0)undecene-7.$CO_2$ sublimates at 68° C.) and regenerated by decomposition to form the original DBA ready for reuse. This is done simply by placing the above complex in a dilute, mineral acid.

The decarboxylation process of the present invention produces the following advantages over older decarboxylation procedures: higher yields are available of the product which has a carbon chain corresponding to the original carboxylic acid, because this new process does not induce pyrolysis; carboxylic acids wherein the carbon chain contains one or more double bonds can be decarboxylated without any change of chemical structure; some carboxylic acids, such as phenoxyacetic acid, can be decarboxylated at room temperature to produce high yields; and the co-reactant for the current process can be regenerated essentially without loss, thus making the new process significantly more economical.

In order to illustrate the process of the present invention, reference is made to the following examples, which, however, are not intended to limit the invention in any respect.

EXAMPLE 1

(a) In a reaction vessel equipped with gas inlet and outlet tubes and a thermometer was placed 10 mmol of lauric acid, 20 mmol of 1,8-diazabicyclo(5,4,0)undecene-7 (hereinafter abbreviated as DBU; manufactured by San-Abbott Ltd. of Kyoto, Japan), and 10 mmol of cuprous bromide, and the mixture was heated for 1 hr at 320° C. while passing nitrogen gas through the reaction vessel. The yield of the desired dodecane was 51% of theory.

(b) In the fashion described, other acids of the general formula $C_nH_{2n+1}COOH$ (n is varied as shown in Table I) were treated at 320°–340° C. for 30 min. to produce the yields shown in line (a) of Table I. When the above reaction is carried out in a multi-step distillation tower and the reaction vessel was heated in an electric furnace to 340°–60° C., the yields obtained were much improved as shown in Table I as line (b).

TABLE I

| n | 11 | 13 | 15 | 17 | 19 | 21 |
|---|----|----|----|----|----|----|
| (a) yield in % | 25 | 50 | 42 | 32 | 30 | 41 |
| (b) Yield in % | 60 | 77 | 80 | 78 | 85 | 80 |

EXAMPLE 2

A mixture of 10 mmol of oleic acid and elaidic acid, 20 mmol of DBU and 10 mmol cuprous bromide was reacted at 320°–350° C. for 30 min. Cis-and trans-9-heptadecenes were obtained in yields of 50% and 60% respectively.

EXAMPLE 3

When methacrylic acid was decarboxylated in the above manner with 2 molar equivalents of DBU and 0.25 molar equivalents of cuprous bromide at 240° C. for 30 min., min., propylene was obtained in a yield of 83% (identified as propylene dibromide boiling at 136° C.).

EXAMPLE 4

Decarboxylating 10 mmol of cinnamic acid with 20 mmol of DBU and 2 mmol of cuprous bromide at 240° C. for 30 min. produced styrene in a yield of 75%.

By replacing the cuprous bromide with cupric chloride, essentially the same results are obtained.

EXAMPLE 5

Using benzoic acid or p-substituted benzoic acids with 2 molar equivalents of DBU and 0.3 molar equivalents of cuprous bromide at 240° C., one obtains the yields shown in Table II which shows the p-substituents:

TABLE II

| Substituent | H | Me | MeO | Cl | $NO_2$ |
|---|---|---|---|---|---|
| Yield in % | 60 | 70 | 60 | 75 | 10 |

EXAMPLE 6

Mono-, di- or tri-phenylacetic acids were reacted with 1.5 molar equivalents of DBU to produce the corresponding toluene, diphenylmethane or triphenylmethane in yields of 80, 100 and 100% respectively. All reactions were carried out over a period of 2 to 3 hrs.

using 240° C., 90° C. and 40° C., respectively, as the average reaction temperature.

EXAMPLE 7

When reacting 10 mmol of benzoylacetic acid with 20 mmol DBU at 25° C. for 3 hrs., phenyl methyl ketone was obtained in a yield of 100% of theory.

By the same method but continuing the reaction for 5 hrs. at 25° C., fluorene-9-carboxylic acid yielded 100% of the corresponding decarboxylated products.

EXAMPLE 8

By heating 5 mmol of 1,10-dodecene dicarboxylic acid with 20 mmol of DBU and 10 mmol of cuprous bromide to 340°-360° C. for 30 min. in an argon atmosphere, n-decane was obtained in a yield of 45% of theory.

In all the above examples, DBU can be replaced by any of the materials listed as illustrations for compounds of structure I. In most instances, the yields obtained of decarboxylated products are within 5 or 10% of those listed above. Also when CuSO4 replaces the cuprous bromide used in some of the above examples, similar yields are obtained. More complicated or more costly cupric or cuprous salts could be employed, but for economic reasons, the less costly cuprous halides, cupric halides, nitrate, acetate or sulfate are preferred over other organic cupric or cuprous salts.

We claim:

1. The process of decarboxylating a carboxylic acid consisting essentially in reacting 1 molar equivalent of said carboxylic acid with 0.8 to 3 molar equivalents of a diazabicyclo alkene and 0 to 20 molar equivalents of a simple copper salt at a temperature of 0° to 400° C. for a period of 0.1 to 50 hrs.

2. The process of claim 1 wherein said temperature is between room temperature and 360° C. and the reaction continues for at least 20 min.

3. The process of claim 1 wherein said diazabicyclo alkene is represented by the formula:

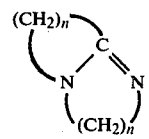

wherein n is 2 to 11 and m is 2 to 6 and each ring may carry one or more loweralkyl substituents.

4. The process of claim 3 wherein said temperature range is from room temperature to 380° C. and the reaction is allowed to proceed for at least 20 min.

5. The process of claim 3 wherein n is 3–5 and m is 2–3.

6. The process of claim 5 wherein n equals 5 and m equals 3.

7. The process of claim 6 wherein the reaction temperature is from room temperature to 380° C. and the reaction proceeds for at least 20 min.

8. The process of claim 1 wherein said copper salt is a copper halide or copper sulfate.

9. The process of claim 8 wherein said copper salt is cuprous bromide or cuprous chloride.

10. The process of decarboxylating a carboxylic acid of the formula R-COOH consisting essentially in reacting one molar equivalent of said carboxylic acid with 1 to 3 molar equivalents of diazabicycloalkene of the formula:

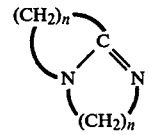

and 0 to 20 molar equivalents of a simple copper salt at a temperature between room temperature and 380° C. for a period of at least 20 min., said R representing a saturated or unsaturated alkyl chain, cycloalkyl, an aromatic or heterocyclic ring or ring system, each optionally carrying one or more carboalkoxy, aryl, styryl, alkoxy, allyloxy, phenoxy, hydroxy, nitro, cyano, halo, acyl, benzoylamino, acylamino, or sulfonic acid groups wherein each acyl or alkyl group includes 1 to 20 carbons, or the corresponding polycarboxylic acids of said R-COOH.

11. The process of claim 10 wherein n is 3–5 and m is 2–3 and said process is carried out in an inert gas stream.

12. The process of claim 11 wherein n is 5 and m is 3.

* * * * *

UNITED STATES PATENT AND TRADEMARK OFFICE
CERTIFICATE OF CORRECTION

PATENT NO. : 4,262,157
DATED : April 14, 1981
INVENTOR(S) : Y. Hori, et al.

It is certified that error appears in the above—identified patent and that said Letters Patent is hereby corrected as shown below:

In column 1, line 30, in Claim 3, and in Claim 10, please change the structure

In other words, the subscript "n" should read "m".

Signed and Sealed this

*Twenty-third* Day of *June 1981*

[SEAL]

*Attest:*

RENE D. TEGTMEYER

*Attesting Officer*  *Acting Commissioner of Patents and Trademarks*